(12) United States Patent
Gerber et al.

(10) Patent No.: US 8,145,323 B2
(45) Date of Patent: Mar. 27, 2012

(54) IMPLANTABLE MEDICAL ELECTRICAL STIMULATION LEAD FIXATION METHOD AND APPARATUS

(75) Inventors: Martin T. Gerber, Maple Grove, MN (US); Eric H. Bonde, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/380,480

(22) Filed: Apr. 27, 2006

(65) Prior Publication Data

US 2007/0255365 A1    Nov. 1, 2007

(51) Int. Cl.
*A61N 1/05* (2006.01)
(52) U.S. Cl. ........................... 607/116; 607/117
(58) Field of Classification Search .................. 607/116, 607/117, 126–129
See application file for complete search history.

(56) References Cited

U.S. PATENT DOCUMENTS

| | | | |
|---|---|---|---|
| 4,414,986 A | 11/1983 | Dickhudt et al. | |
| 4,419,819 A | 12/1983 | Dickhudt et al. | |
| 4,465,079 A | 8/1984 | Dickhudt | |
| 4,519,403 A * | 5/1985 | Dickhudt | 607/117 |
| 5,003,992 A | 4/1991 | Holleman et al. | |
| 5,090,422 A | 2/1992 | Dahl et al. | |
| 5,129,404 A | 7/1992 | Spehr et al. | |
| 5,207,672 A * | 5/1993 | Roth et al. | 606/10 |
| 5,215,105 A * | 6/1993 | Kizelshteyn et al. | 128/898 |
| 5,366,490 A * | 11/1994 | Edwards et al. | 607/99 |
| 5,387,233 A | 2/1995 | Alferness et al. | |
| 5,456,667 A | 10/1995 | Ham et al. | |
| 5,484,445 A | 1/1996 | Knuth | |
| 5,531,779 A | 7/1996 | Dahl et al. | |
| 5,545,193 A * | 8/1996 | Fleischman et al. | 607/99 |
| 5,723,718 A * | 3/1998 | Berens | 800/10 |
| 5,865,843 A | 2/1999 | Baudino | |
| 5,957,965 A | 9/1999 | Moumane et al. | |
| 5,957,966 A | 9/1999 | Schroeppel et al. | |
| 6,055,457 A | 4/2000 | Bonner | |
| 6,077,298 A | 6/2000 | Tu et al. | |
| 6,104,960 A | 8/2000 | Duysens et al. | |
| 6,161,029 A | 12/2000 | Spreigl et al. | |
| 6,322,559 B1 | 11/2001 | Daulton et al. | |
| 6,325,797 B1 | 12/2001 | Stewart et al. | |
| 6,388,043 B1 | 5/2002 | Langer et al. | |
| 6,510,347 B2 * | 1/2003 | Borkan | 607/117 |

(Continued)

FOREIGN PATENT DOCUMENTS

CA    2527976 A1    7/2006

(Continued)

OTHER PUBLICATIONS

Lendlein, "Shape Memory Polymers—Biodegradable Sutures", Abstracted from Materials World, Jul. 2002, 10:7, p. 29-30, Website Article: www.azom.com/details.asp?articleID=1542.

(Continued)

*Primary Examiner* — Niketa Patel
*Assistant Examiner* — Joseph Stoklosa

(57) ABSTRACT

An implantable medical electrical lead for electrical stimulation of body tissue that includes at least one electrode; a lead body; and at least one modifiable portion wherein the at least one modifiable portion can exist in both a deflated configuration and an inflated configuration, and wherein the inflated configuration exhibits a greater resistance to movement of the lead within the body tissue than does the deflated configuration. Kits, systems, and methods of using the leads are also included.

20 Claims, 17 Drawing Sheets

U.S. PATENT DOCUMENTS

| | | | |
|---|---|---|---|
| 6,704,604 B2 | 3/2004 | Soukup et al. | |
| 6,711,443 B2 | 3/2004 | Osypka | |
| 6,720,402 B2 | 4/2004 | Langer et al. | |
| 6,814,733 B2* | 11/2004 | Schwartz et al. | 606/41 |
| 6,909,920 B2 | 6/2005 | Thompson | |
| 6,952,613 B2 | 10/2005 | Swoyer et al. | |
| 6,999,819 B2 | 2/2006 | Swoyer et al. | |
| 7,099,718 B1* | 8/2006 | Thacker et al. | 607/117 |
| 7,107,105 B2 | 9/2006 | Bjorklund et al. | |
| 7,155,293 B2 | 12/2006 | Westlund et al. | |
| 7,272,448 B1 | 9/2007 | Morgan et al. | |
| 2002/0077684 A1* | 6/2002 | Clemens et al. | 607/116 |
| 2002/0095114 A1* | 7/2002 | Palasis | 604/96.01 |
| 2002/0147485 A1 | 10/2002 | Mamo et al. | |
| 2003/0050681 A1 | 3/2003 | Pianca et al. | |
| 2003/0199961 A1 | 10/2003 | Bjorklund et al. | |
| 2004/0176782 A1 | 9/2004 | Hanse et al. | |
| 2004/0215237 A1 | 10/2004 | Christopherson et al. | |
| 2004/0230279 A1 | 11/2004 | Cates et al. | |
| 2004/0230280 A1 | 11/2004 | Cates et al. | |
| 2004/0230281 A1 | 11/2004 | Heil et al. | |
| 2005/0038491 A1 | 2/2005 | Haack | |
| 2005/0060014 A1 | 3/2005 | Swoyer et al. | |
| 2005/0096718 A1 | 5/2005 | Gerber et al. | |
| 2005/0288781 A1 | 12/2005 | Moaddeb et al. | |
| 2006/0041089 A1 | 2/2006 | Mather et al. | |
| 2006/0079949 A1 | 4/2006 | Hine et al. | |
| 2006/0247753 A1 | 11/2006 | Wenger et al. | |
| 2007/0073130 A1 | 3/2007 | Finch et al. | |
| 2007/0255366 A1 | 11/2007 | Gerber | |
| 2007/0255383 A1 | 11/2007 | Gerber | |
| 2007/0261115 A1 | 11/2007 | Gerber | |

FOREIGN PATENT DOCUMENTS

| | | |
|---|---|---|
| EP | 861676 | 2/1998 |
| WO | WO-02087690 | 11/2002 |
| WO | WO-2004047914 | 6/2004 |

OTHER PUBLICATIONS

Wingfield, "Shape Change Materials", Feb. 2006: 13:08, Website Article: www.loop.ph/twiki/bin/view/Openloop/ShapeChange.
Lendlein, et al. Biodegradable, Elastic Shape-Memory Polymers for Potential Biomedical Application, Science, May 2002, 296:5573, p. 1673-1676.
Gerber, Implantable Medical Electrical Stimulation Lead Fixation Method and Apparatus, U.S. Appl. No. 11/380,499, Final Office Action May 28, 2009.
Gerber, Implantable Medical Electrical Stimulation Lead Fixation Method and Apparatus, U.S. Appl. No. 11/380,499, Non-Final Office Action Nov. 26, 2008.
Gerber, Implantable Medical Electrical Stimulation Lead Fixation Method and Apparatus, U.S. Appl. No. 11/380,499, Advisory Action Jul. 17, 2008.
Gerber, Implantable Medical Electrical Stimulation Lead Fixation Method and Apparatus, U.S. Appl. No. 11/380,499, Final Office Action Apr. 29, 2008.
Gerber, Implantable Medical Electrical Stimulation Lead Fixation Method and Apparatus, U.S. Appl. No. 11/380,499, Non-Final Office Action Aug. 28, 2007.
Gerber, Implantable Medical Electrical Stimulation Lead Fixation Method and Apparatus, U.S. Appl. No. 11/380,493, Final Office Action Aug. 25, 2009.
Gerber, Implantable Medical Electrical Stimulation Lead Fixation Method and Apparatus, U.S. Appl. No. 11/380,493, Non-Final Office Action Feb. 27, 2009.
Gerber, Implantable Medical Electrical Stimulation Lead Fixation Method and Apparatus, U.S. Appl. No. 11/380,493, Final Office Action Oct. 6, 2008.
Gerber, Implantable Medical Electrical Stimulation Lead Fixation Method and Apparatus, U.S. Appl. No. 11/380,493, Non-Final Office Action Feb. 12, 2008.
Gerber et al., Implantable Medical Electrical Stimulation Lead Fixation Method and Apparatus, U.S. Appl. No. 11/380,511, Non-Final Office Action Mar. 5, 2009.
Gerber et al., Implantable Medical Electrical Stimulation Lead Fixation Method and Apparatus, U.S. Appl. No. 11/380,511, Advisory Action Oct. 30, 2008.
Gerber et al., Implantable Medical Electrical Stimulation Lead Fixation Method and Apparatus, U.S. Appl. No. 11/380,511, Final Office Action Jul. 28, 2008.
Gerber et al., Implantable Medical Electrical Stimulation Lead Fixation Method and Apparatus, U.S. Appl. No. 11/380,511, Non-Final Office Action Nov. 15, 2007.
U.S. Appl. No. 11/380,499 Office Action dated Nov. 30, 2009.
U.S. Appl. No. 11/380,493 Office Action dated Dec. 7, 2009.
U.S. Appl. No. 11/380,511 Non-Final Office Action dated Oct. 30, 2009.
U.S. Appl. No. 11/380,499 Office Action dated Nov. 30, 2009.
U.S. Appl. No. 11/380,499 response filed Feb. 27, 2010.
U.S. Appl. No. 11/380,499 Office Action dated Jun. 11, 2010.
U.S. Appl. No. 11/380,499 response filed Jul. 17, 2008.
U.S. Appl. No. 11/380,499 response filed Jan. 28, 2008.
U.S. Appl. No. 11/380,499 response filed Jun. 28, 2008.
U.S. Appl. No. 11/380,499 response filed Feb. 26, 2009.
U.S. Appl. No. 11/380,499 response filed Aug. 28, 2009.
U.S. Appl. No. 11/380,493 response filed Aug. 25, 2010.
U.S. Appl. No. 11/380,493 Final Office Action dated Jun. 25, 2010.
U.S. Appl. No. 11/380,493 response filed Nov. 25, 2009.
U.S. Appl. No. 11/380,493 response filed May 22, 2009.
U.S. Appl. No. 11/380,493 response filed Jan. 6, 2009.
U.S. Appl. No. 11/380,493 supplemental response filed Sep. 22, 2008.
U.S. Appl. No. 11/380,493 response filed May 12, 2008.
U.S. Appl. No. 11/380,493 response filed Mar. 5, 2010.
U.S. Appl. No. 11/380,493 Office Action dated Dec. 7, 2009.
U.S. Appl. No. 11/380,511 response filed Aug. 2, 2010.
U.S. Appl. No. 11/380,511 Office Action dated May 3, 2010.
U.S. Appl. No. 11/380,511 response filed Feb. 1, 2010.
U.S. Appl. No. 11/380,511 response filed Apr. 15, 2008.
U.S. Appl. No. 11/380,511 response filed Sep. 28, 2008.
U.S. Appl. No. 11/380,511 response filed Dec. 30, 2008.
U.S. Appl. No. 11/380,511 response filed Jul. 4, 2009.
U.S. Appl. No. 11/380,511 Final Office Action dated Jul. 28, 2008.
U.S. Appl. No. 11/380,511 Office Action dated Nov. 15, 2007.
U.S. Appl. No. 11/380,499 Response filed Sep. 10, 2010.
U.S. Appl. No. 11/380,499 Final Office Action dated Dec. 1, 2010.
U.S. Appl. No. 11/380,499 Response filed Mar. 1, 2011.
U.S. Appl. No. 11/380,499 Non-Final Office Action dated Mar. 31, 2011.
U.S. Appl. No. 11/380,499 Response filed Jun. 30, 2011.
U.S. Appl. No. 11/380,493 Advisory Action dated Oct. 1, 2010.
U.S. Appl. No. 11/380,493 RCE Response filed Nov. 24, 2010.
U.S. Appl. No. 11/380,511 Final Office Action dated Dec. 2, 2010.
U.S. Appl. No. 11/380,511 RCE Response filed Feb. 14, 2011.
U.S. Appl. No. 11/380,499 Notice of Allowance dated Nov. 3, 2011.

* cited by examiner

IMPLANTABLE MEDICAL ELECTRICAL STIMULATION LEAD FIXATION METHOD AND APPARATUS

FIELD OF THE INVENTION

This invention relates generally to device for electrical stimulation of body tissue. More specifically, this invention relates to an implantable medical electrical lead having at least one stimulation electrode and a fixation mechanism for fixing the lead within the tissue.

BACKGROUND OF THE INVENTION

Pelvic floor disorders such as, urinary incontinence, urinary urge/frequency, urinary retention, pelvic pain, bowel dysfunction (constipation, diarrhea), and erectile dysfunction, involve bodily functions that are influenced by the sacral nerves. Specifically, urinary incontinence is the involuntary control over the bladder that is exhibited in various patients. Urinary incontinence is primarily treated through pharmaceuticals and surgery. Many of the pharmaceuticals do not adequately resolve the issue and can cause unwanted side effects, and a number of the surgical procedures have a low success rate and are not reversible. Several other methods have been used to control urinary incontinence, for example, vesicostomy or an artificial sphincter implanted around the urethra. These solutions have drawbacks well known to those skilled in the art. In addition, the other mentioned disorders do not have adequate pharmaceutical or surgical treatment options.

The organs involved in bladder, bowel, and sexual function receive much of their control via the sacral nerves, in some instances the second, third, and fourth sacral nerves, commonly referred to as S2, S3 and S4 respectively. Electrical stimulation of these various nerves has been found to offer some control over these functions.

Neurostimulation leads with at least one stimulation electrode positioned on or near the sacral nerves of the human body have been implanted to provide partial control for urinary incontinence. Temporary sacral nerve stimulation is accomplished through implantation of a temporary neurostimulation lead extending through the skin and connected with a temporary external pulse generator as described for example in commonly assigned U.S. Pat. Nos. 5,957,965 and 6,104,960. A permanent neurostimulator can be implanted if the temporary stimulation is efficacious and it is possible to do so in the particular patient. Permanent implantation can be accomplished by implanting a permanent neurostimulation lead, extending the proximal portion of the lead body subcutaneously, and connecting its proximal end with an implantable pulse generator (IPG) implanted subcutaneously.

One problem that can be associated with implantation of both permanent and temporary neurostimulation leads involves maintaining the electrode(s) in casual contact, that is in a location where slight contact of the electrode with the sacral nerve may occur or in close proximity to the sacral nerve to provide adequate stimulation of the sacral nerve, while allowing for some axial movement of the lead body. In order to minimize the movement of the lead, the lead body is fixed to retard migration and dislodgement of the electrodes from the optimal position. This can be accomplished by employing sutures or a sacral lead fixation mechanism, an example of which is described in commonly assigned U.S. Pat. No. 5,484,445. An example of a lead that includes a fixation mechanism can be found in commonly assigned U.S. Pat. No. 6,999,819, the disclosure of which is incorporated herein by reference.

Although the fixation mechanisms of the above referenced patents are a significant advance over the prior art, there are still further advantages to be gained. Therefore, there remains a need for leads having other fixation mechanisms.

SUMMARY OF THE INVENTION

The invention includes an implantable medical electrical lead for electrical stimulation of body tissue that includes at least one electrode; a lead body; and at least one modifiable portion wherein the at least one modifiable portion can exist in both a deflated configuration and an inflated configuration, and wherein the inflated configuration exhibits a greater resistance to movement of the lead within the body tissue than does the deflated configuration.

The invention also includes a kit that includes an implantable medical electrical lead for electrical stimulation of body tissue that includes at least one electrode; a lead body having at least a fluid conduit; at least one modifiable portion wherein the at least one modifiable portion can exist in both a deflated configuration and an inflated configuration, wherein the inflated configuration exhibits a greater resistance to movement of the lead within the body tissue than does the deflated configuration, and wherein the fluid conduit of the lead body functions as a conduit for fluid between the modifiable portion and an area outside the lead; and an apparatus for introducing fluid into the fluid conduit.

The invention further includes a medical electrical stimulation system including an implantable pulse generator for providing medical electrical stimulation; and an implantable medical electrical lead for electrical stimulation of body tissue that includes at least one electrode; a lead body; at least one modifiable portion wherein the at least one modifiable portion can exist in both a deflated configuration and an inflated configuration, wherein the inflated configuration exhibits a greater resistance to movement of the lead within the body tissue than does the deflated configuration.

Also included is a method of providing electrical stimulation of body tissue at a stimulation site employing an implantable pulse generator including providing an implantable medical lead that includes at least one electrode a lead body comprising at least a fluid conduit; at least one modifiable portion wherein the at least one modifiable portion can exist in both a deflated configuration and an inflated configuration, wherein the inflated configuration exhibits a greater resistance to movement of the lead within the body tissue than does the deflated configuration, and wherein the fluid conduit of the lead body functions as a conduit for fluid between the modifiable portion and an area outside the lead; and at least one proximal connector element formed in a connector array in a proximal segment of the lead body; percutaneously introducing the implantable medical lead adjacent to the stimulation site; adding fluid to the fluid conduit to transition the at least one modifiable portion from the deflated configuration to the inflated configuration; and coupling the at least one proximal connector element with the implantable pulse generator.

The full range of advantages and features of this invention are only appreciated by a full reading of this specification and a full understanding of the invention. Therefore, to complete this specification, a detailed description of the invention and the preferred embodiments follow, after a brief description of the drawings, wherein additional advantages and features of the invention are disclosed.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Embodiments of the invention are illustrated in the drawings, wherein like reference numerals refer to like elements in the various views. Furthermore, it will be understood by one of skill in the art that the drawings are not drawn to scale.

DETAILED DESCRIPTION OF THE INVENTION

A lead in accordance with the invention can be utilized to provide neurostimulation or neuromodulation to any portion of the nervous system within the body of a patient. In one embodiment a lead in accordance with the invention can be utilized in any target tissue that requires some amount of fixation or traction to minimize movement of the lead. In one embodiment the lead can be implanted within muscle or connective tissue to stimulate or modulate peripheral nerves within that tissue.

A lead in accordance with the invention can be placed anywhere within the body where electrical stimulation is desired. In one embodiment a lead in accordance with the invention can be utilized to provide neurostimulation within the pelvic region of a patient. In such an embodiment the lead may be positioned to provide stimulation to one or more of the sacral nerves. Sacral nerves that may be stimulated using a lead in accordance with the invention include, but are not limited to the pudendal nerve, the pelvic splanchnic nerve, the cavernosa nerve in the penis or nerves located in or near the clitoris in a female, the hypogastric nerve, the vesicle nerve plexus, the perineal nerves, the pelvic nerve plexus, the prostate gland, the prostatic plexus nerve, the vagina, the anus, the urethra, the penis dorsal nerve, the inferior rectal nerves, the scrotal nerves, scrotum, Alcock's Canal, the sacro-tuberous ligament, the ischial tuberosity, the greater sciatic foramen, the lesser sciatic foramen, and other nerves or nerve portions located in the general region of the pelvic floor.

Neurostimulation using a lead in accordance with the invention can be utilized to treat any of a number of conditions including, but not limited to pelvic floor disorders such as urinary control disorders, fecal control disorders, sexual dysfunction, pelvic pain, interstitial cystitis, endometriosis, and genital pain such as vulvodynia or idiopathic chronic testicular pain. Although the invention is discussed with respect to stimulation of one or more nerves within the pelvic floor for the treatment of urinary incontinence, it will be understood by one of skill in the art, that leads of the invention can be utilized to treat other disorders or conditions by stimulating other nerves.

In one embodiment, a lead in accordance with the invention can be used with a therapy for treating urinary incontinence, such as MEDTRONIC INTERSTIM® Therapy. For example, an implantable neurostimulation system may stimulate organs involved in urinary, fecal or sexual function via C-fibers or sacral nerves at the second, third, and fourth sacral nerve positions, commonly referred to as S2, S3, and S4, respectively. In another embodiment a lead in accordance with the invention can be used with a therapy for treating gastroparesis, such as MEDTRONIC ENTERRA® Therapy.

Figure 1A:
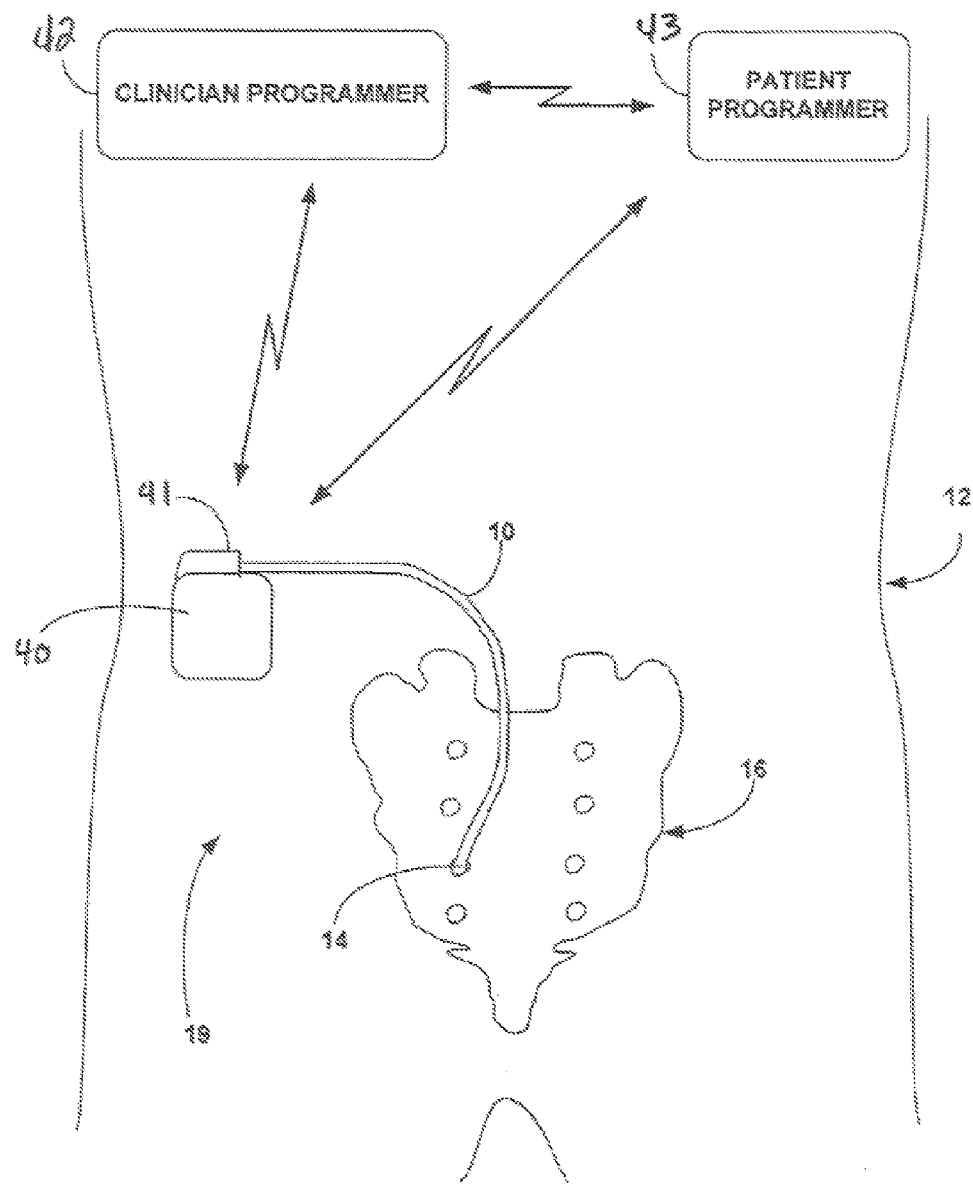
FIG. 1A is a diagram illustrating an implantable neurostimulator system for stimulating nerves, such as sacral nerves via a lead.

FIG. 1A is a diagram illustrating an implantable neurostimulation system 19 for stimulating a nerve, such as a sacral nerve, via lead 10. Lead 10 is generically depicted in FIG. 1A, and does not necessarily depict all of the features of a lead in accordance with the invention. Neurostimulation system 19 delivers neurostimulation to the sacral nerves or other regions of the nervous system known to treat pelvic floor disorders, urinary control disorders, fecal control disorders, interstitial cystitis, sexual dysfunction, and pelvic pain. Again, neurostimulation system 19 and lead 10 may be useful in other neurostimulation applications, such as spinal cord stimulation, deep brain stimulation, gastric stimulation, and the like. As shown in FIG. 1A, system 19 includes lead 10 and an implantable neurostimulator 40. In addition, a proximal end 32 of stimulation lead 10 may be coupled to a connector block 41 associated with neurostimulator 40. The lead 10 also has a distal end 31 (not visible in FIG. 1A, but seen in FIGS. 1B, 1C, and 1D).

Neurostimulator 40 includes an implantable pulse generator, and delivers neurostimulation therapy to patient 12 in the form of electrical pulses generated by the implantable pulse generator. In the example of FIG. 1A, neurostimulator 40 is implanted in the upper left buttock of patient 12, but may be implanted at other locations. An example of a commercially available neurostimulator includes, but is not limited to MEDTRONIC® Model 3023 Neurostimulator.

Lead 10 carries one or more stimulation electrodes, for example, 1 to 8 electrodes, to permit delivery of electrical stimulation to sacral nerves. Embodiments of the invention may have 1, 2, 3, 4, 5, 6, 7, 8 or more electrodes. The at least one electrode 30 can include ring electrodes, coil electrodes, circumferential segment electrodes, or any combination thereof. One embodiment of a lead in accordance with the invention has at least two (2) electrodes. Another embodiment of a lead in accordance with the invention has at least four (4) electrodes. In one embodiment having at least four electrodes, at least one of those electrodes can be a coil electrode. In another embodiment of the invention having at least four electrodes, at least one electrode is a coil electrode and at least one of the other electrodes is a ring electrode.

The at least one electrode 30 can be made of any commonly utilized material as is known to those of skill in the art. In one embodiment the at least one electrode 30 is made of a solid surface, bio-compatible material, examples of such materials include, but are not limited to, platinum, a platinum-iridium alloy, or stainless steel for example. Also, in some embodiments, lead 10 may carry one or more electrodes capable of sensing one or more parameters to permit neurostimulator 40 to sense electrical signals within sacrum 16, for example. In some embodiments, neurostimulator 40 may be coupled to two or more leads deployed at different positions, for example, relative to the spinal cord or sacral nerves.

In one embodiment lead 10 includes a lead body that contains one or more conductors to electrically couple the one or more electrodes to terminals within neurostimulator 40. In one embodiment the outer diameter of the lead body, referred to herein as the lead body diameter can be from about 0.5 mm to about 2 mm. In yet another embodiment, the lead body diameter can be about 1 mm to about 1.5 mm. In a further embodiment the lead body diameter can be about 1.3 mm.

Leads in accordance with the invention can have variable lengths, depending at least in part on considerations such as the type of tissue that the lead is to be implanted in, the surrounding anatomy where the lead will be implanted, the particular configuration of the lead, the number of modifiable portions within the lead, the number of electrodes within the lead, the location of the one or more modifiable portions and/or the one or more electrodes within the lead, whether or not the lead will be used with an extension, and where the neurostimulator is to be implanted, for example.

In one embodiment of the invention, where the lead is to be used for stimulation of the pelvic floor with a lead extension, the length of the lead can range from about 10 cm to about 100 cm. In another embodiment of the invention, where the lead is to be used for stimulation of the pelvic floor with a lead extension, the length of the lead can range from about 10 cm to about 80 cm. In yet another embodiment of the invention, where the lead is to be used for stimulation of the pelvic floor with a lead extension, the length of the lead can range from about 20 cm to about 60 cm.

Figure 1B:
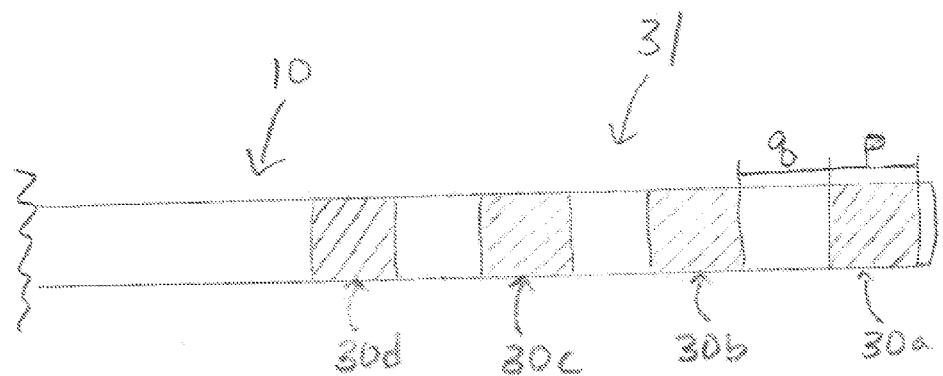
FIG. 1B is a diagram illustrating a portion of a lead in accordance with the invention.

In one embodiment, the at least one electrode 30 is located towards the distal end 31 of the lead 10. FIG. 1B depicts a portion of an exemplary lead 10 in accordance with the invention. The exemplary lead 10 depicted there includes four electrodes 30a, 30b, 30c, and 30d. The electrodes 30a, 30b, 30c, and 30d have an electrode length p. In this example, the four electrodes 30a, 30b, 30c, and 30d have equal electrode lengths p. One of skill in the art, having read this specification, will understand that the electrode lengths p could be different or the same. One of skill in the art will also understand that the electrode lengths p of any one electrode or all of the electrodes can vary and may be at least in part dependent on a number of factors including, but not limited to the type of tissue that the lead will be implanted in, the surrounding anatomy where the lead will be implanted, the stimulation parameters that the lead will be delivering, the types of electrodes, and the number of electrodes.

In one embodiment, the electrode length p can range from about 1 mm to about 20 mm. In another embodiment the electrode length p can range from about 1 mm to about 3 mm. In yet another embodiment the electrode length p can range from about 3 mm to about 10 mm. In one embodiment, a lead 10 has at least one electrode that has an electrode length p of about 3 mm. In another embodiment, a lead 10 has at least one electrode that has an electrode length p of about 10 mm.

The electrodes 30a, 30b, 30c, and 30d are separated by inter-electrode distances q. In this example, the four electrodes 30a, 30b, 30c, and 30d are separated by equal inter-electrode distances q, but one of skill in the art, having read this specification, will understand that the inter-electrode distances q could be different. One of skill in the art, having read this specification, will also understand that the inter-electrode distances q of any one electrode or all of the electrodes can vary and may be at least in part dependent on a number of factors including, but not limited to the type of tissue that the lead will be implanted in, the surrounding anatomy where the lead will be implanted, the stimulation parameters that the lead will be delivering, the types of electrodes, and the number of electrodes.

In one embodiment, the inter-electrode distances q can range from about 0.5 mm to about 5 mm. In another embodiment the inter-electrode distances q can range from about 1 mm to about 2 mm. In yet another embodiment the inter-electrode distances q can range from about 1.2 mm to about 1.6 mm. In one embodiment, a lead 10 has at least two electrodes that have an inter-electrode distance q of about 1.5 mm. In another embodiment, a lead 10 has at least two electrodes that have an inter-electrode distance q of about 3 mm.

Figure 1C:
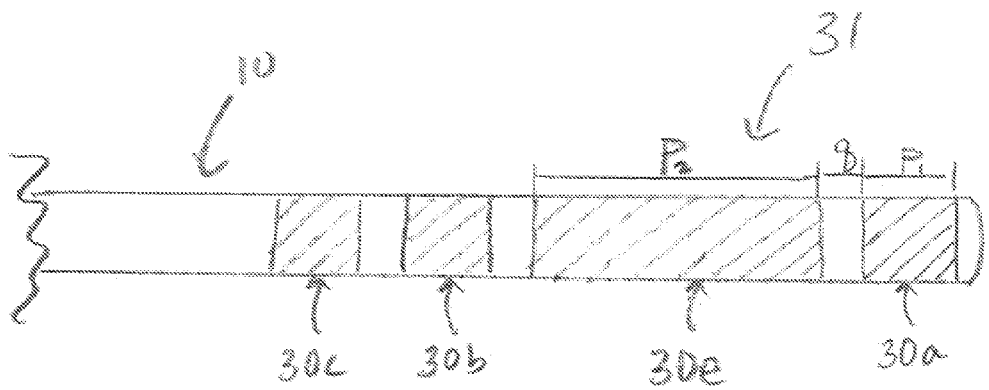
FIG. 1C is a diagram illustrating a portion of a lead in accordance with the invention.

The exemplary lead depicted in FIG. 1C also includes four electrodes 30a, 30b, 30c, and 30e in which only three of the electrodes 30a, 30b, and 30c have the same electrode lengths $p_1$, and the fourth electrode 30e has a different electrode length $p_2$. One of skill in the art, having read this specification, will understand that any combination of equal and unequal electrode lengths $p_1$-$p_2$ are included within the scope of this invention. In one embodiment of the invention, a lead includes four ring electrodes with the same electrode lengths p. In another embodiment of the invention, a lead includes three ring electrodes with the same electrode lengths p and one coil electrode with a different electrode length p.

The at least one electrode can be electrically coupled to the distal end of a coiled wire lead conductor within the body of the lead. The proximal ends of the separately insulated lead conductors can each be coupled to respective connector elements, for example ring-shaped connector elements, in a proximal connector element array in the body of the lead. In one embodiment, the conductor wires can be formed of an MP35N alloy and are insulated from one another within an insulating polymer sheath such as polyurethane, fluoropolymer or silicone rubber for example. The lead conductor wires can be separately insulated by an insulation coating and can be wound in a quadra-filar manner having a common winding diameter within the outer sheath. The coil formed by the coiled wire conductors defines a lead body lumen of the lead body. It will be understood that a further inner tubular sheath could be interposed within the aligned wire coils to provide the lead body lumen.

The connector elements can be adapted to be coupled with a neurostimulator IPG, additional intermediate wiring, or other stimulation device adapted to be implanted subcutaneously. An example of such an implantable pulse generator is the MEDTRONIC® Neurostimulator Model 3023. Electrical stimulation pulses generated by the neurostimulator IPG are applied to a nerve or nerves, such as the sacral nerve, through the at least one electrode in either a unipolar or bipolar stimulation mode.

As further shown in FIG. 1A, implantable neurostimulation system 19 also may include a clinician programmer 42 and a patient programmer 43. Clinician programmer 42 may be a handheld computing device that permits a clinician to program neurostimulation therapy for patient 12, e.g., using input keys and a display. For example, using clinician programmer 42, the clinician may specify neurostimulation parameters for use in delivery of neurostimulation therapy.

Clinician programmer 42 supports radio frequency telemetry with neurostimulator 40 to download neurostimulation parameters and, optionally, upload operational or physiological data stored by neurostimulator. In this manner, the clinician may periodically interrogate neurostimulator 40 to evaluate efficacy and, if necessary, modify the stimulation parameters.

Like clinician programmer 42, patient programmer 43 may be a handheld computing device. Patient programmer 43 may also include a display and input keys to allow patient 12 to interact with patient programmer 43 and implantable neurostimulator 40. In this manner, patient programmer 43 provides patient 12 with an interface for control of neurostimulation therapy by neurostimulator 40.

For example, patient 12 may use patient programmer 43 to start, stop or adjust neurostimulation therapy. In particular, patient programmer 43 may permit patient 12 to adjust stimulation parameters such as duration, amplitude, pulse width and pulse rate, within an adjustment range specified by the clinician via clinician programmer 42.

Neurostimulator 40, clinician programmer 42 and patient programmer 43 may communicate via wireless communication, as shown in FIG. 1A. Clinician programmer 42 and patient programmer 43 may, for example, communicate via wireless communication with neurostimulator 40 using RF telemetry techniques known in the art. Clinician programmer 42 and patient programmer 43 also may communicate with each other using any of a variety of local wireless communication techniques, such as RF communication according to the 802.11 or Bluetooth specification sets, or other standard or proprietary telemetry protocols.

Figure 1D:
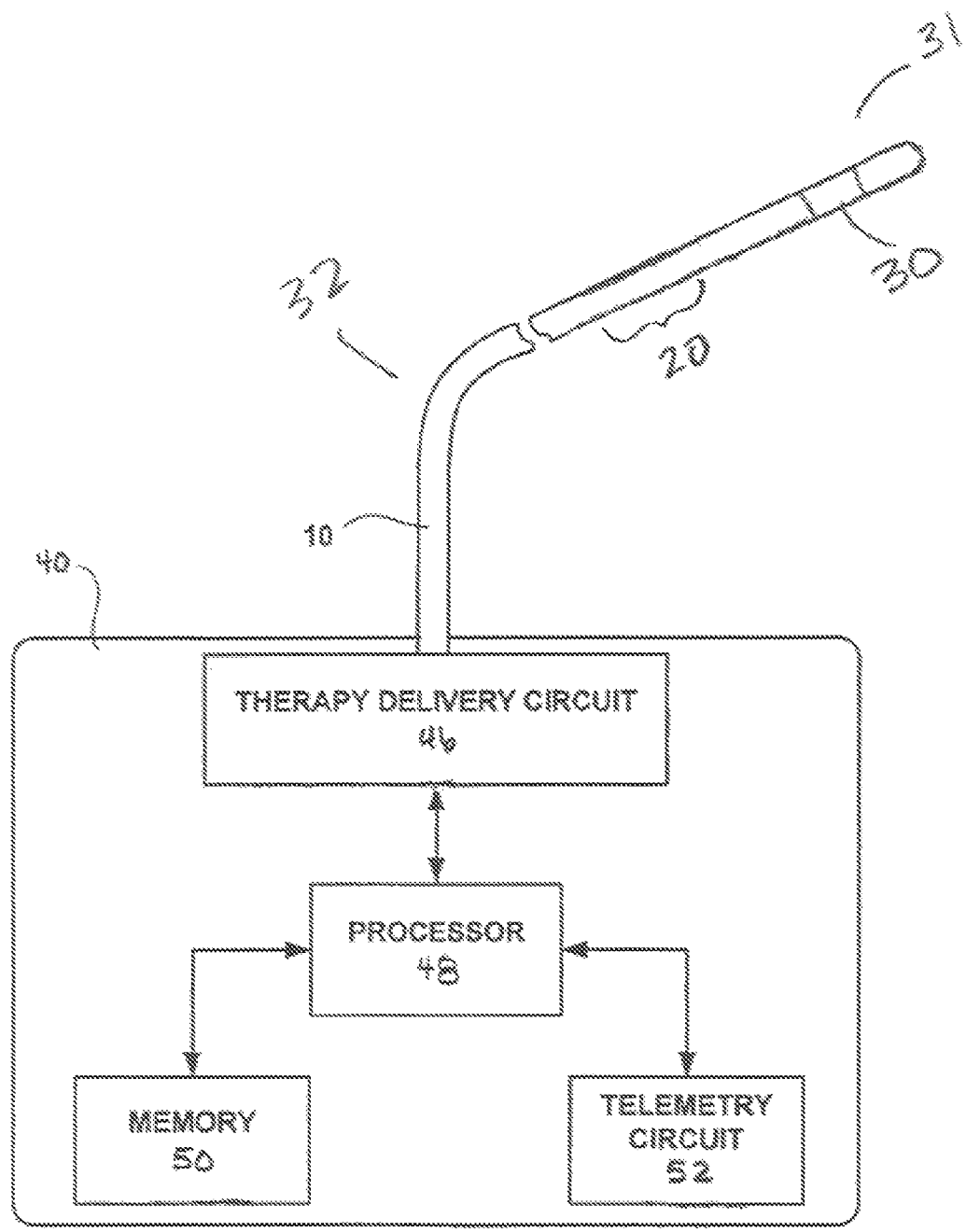
FIG. 1D is a block diagram illustrating various components of an implantable neurostimulator with an implantable lead incorporating a fixation mechanism.

FIG. 1D is a block diagram illustrating various components of an implantable neurostimulator 40 incorporating an implantable lead 10 with a modifiable portion 20. As shown in FIG. 1D, neurostimulator 40 delivers neurostimulation therapy via at least one electrode 30 of lead 10. Electrode 30 is electrically coupled to a therapy delivery circuit 46 via conductors within lead 10. Therapy delivery circuit 46 may, for example, include an implantable pulse generator coupled to a power source such as a battery. The implantable pulse generator within therapy delivery circuit 46 delivers electrical pulses to patient 12 via the at least one electrode 30 under the control of a processor 48.

Processor 48 controls the implantable pulse generator within therapy delivery circuit 46 to deliver neurostimulation therapy according to selected stimulation parameters. In one embodiment, processor 48 can control therapy delivery circuit 46 to deliver electrical pulses with selected amplitudes, pulse widths, rates, or some combination thereof as specified by the program(s). In addition, processor 48 can also control therapy delivery circuit 46 to deliver the neurostimulation pulses via selected subsets of one or more electrodes 30 with selected polarities.

Processor 48 may control therapy delivery circuit 46 to deliver each pulse according to a different program, thereby interleaving programs to simultaneously treat different symptoms or provide a combined therapeutic effect. For example, in addition to treatment of one symptom such as sexual dysfunction, neurostimulator 40 may be configured to deliver neurostimulation therapy to treat other symptoms such as pain or incontinence. Processor 48 may include a microprocessor, a controller, a digital signal processor (DSP), an application-specific integrated chip (ASIC), a field-programmable gate array (FPGA), discrete logic circuitry, or the like.

Neurostimulator 40 also includes a memory 50. In some embodiments, memory 50 stores multiple sets of stimulation parameters that are available to be selected by patient 12 for delivery of neurostimulation therapy to the patient 12. For example, memory 50 may store stimulation parameters transmitted by clinician programmer 42.

Memory 50 also stores program instructions that, when executed by processor 48, cause neurostimulator 40 to deliver neurostimulation therapy. Memory 50 may include any volatile or non-volatile media, such as random access memory (RAM), random read-only memory (ROM), compact disc-read-only memory (CD-ROM), non-volatile random access memory (NVRAM), electrically erasable programmable read-only memory (EEPROM), flash memory, and the like. Accordingly, computer-readable media storing instructions may be provided to cause processor 48 to provide functionality as described herein.

In some embodiments a telemetry circuit 52 can support wireless communication between two or more of neurostimulator 40, clinician programmer 42, and patient programmer 43. In addition, in some embodiments, telemetry circuit 52 supports wireless communication with one or more wireless sensors that sense physiological signals and transmit the signals to neurostimulator 40 clinician programmer 42, patient programmer 43 or some combination thereof.

As mentioned above, migration of lead 10 can have detrimental effects on the efficacy of neurostimulation therapy for a patient 12. Fixing the neurostimulation lead 10 to surrounding tissue may prevent harmful effects that may result from a loose neurostimulation lead 10. As described below, a lead in accordance with the invention may provide fixation (not shown in FIGS. 1A through 1D) between the lead 10 and tissue surrounding the lead 10, such as tissue within the sacrum 16, without the need for surgical implantation techniques, such as sutures.

Leads in accordance with the invention can be utilized for electrical stimulation of body tissue and include at least one modifiable portion, that has a deflated configuration and an inflated configuration wherein the inflated configuration of the modifiable portion exhibits a greater resistance to movement of the lead within the body tissue than does the deflated configuration. The inflated configuration generally provides increased resistance to movement of the lead within the body tissue because of its larger size and/or increased surface area that interacts with the surrounding tissue.

In one embodiment, the deflated configuration of the modifiable potion is coaxial with and has substantially the same diameter and configuration as an adjacent portion of the lead body. In another embodiment, the deflated configuration of the modifiable portion is coaxial with and has substantially the same diameter, but a different configuration than an adjacent portion of the lead body. In another embodiment the modifiable portion is formed from the same kind but a different piece of material, and in yet another embodiment the modifiable portion is formed from a different kind of material. In such embodiments the modifiable portion can be secured to the remainder of the lead body as would be known to one of skill in the art, having read this specification.

Both the modifiable portion and the lead body have diameters, referred to herein as the modifiable portion diameter and the lead body diameter respectively. The lead body diameter is generally considered as the diameter of the lead body directly adjacent to the modifiable portion. In one embodiment of the invention, the diameter of the deflated configuration of the modifiable portion and the lead body diameter are substantially equal. In another embodiment, the diameter of the deflated configuration of the modifiable portion diameter is less than the lead body diameter. The diameter of the inflated configuration is greater than the lead body diameter. In one embodiment, the diameter of the inflated configuration is at least about 50% bigger than the lead body diameter. In another embodiment, the diameter of the inflated configuration is at least about 100% bigger than the lead body diameter. In yet another embodiment, the diameter of the inflated configuration is at least about 150% bigger than the lead body diameter.

In one embodiment of the invention, the modifiable portion is made of one or more materials that is capable of being resiliently inflated. In one embodiment the modifiable portion is made of an elastomeric material that is biocompatible. Examples of materials that can be used to make the at least one modifiable portion include, but are not limited to, silicone, polyurethane, polypropylene, polyamide, and polyester. In one embodiment, the at least one modifiable portion is made of polyurethane. In one embodiment, the material that the modifiable portion is made of can incorporate a visualization agent to allow location of the modifiable portion using visualization techniques.

Figure 2A:
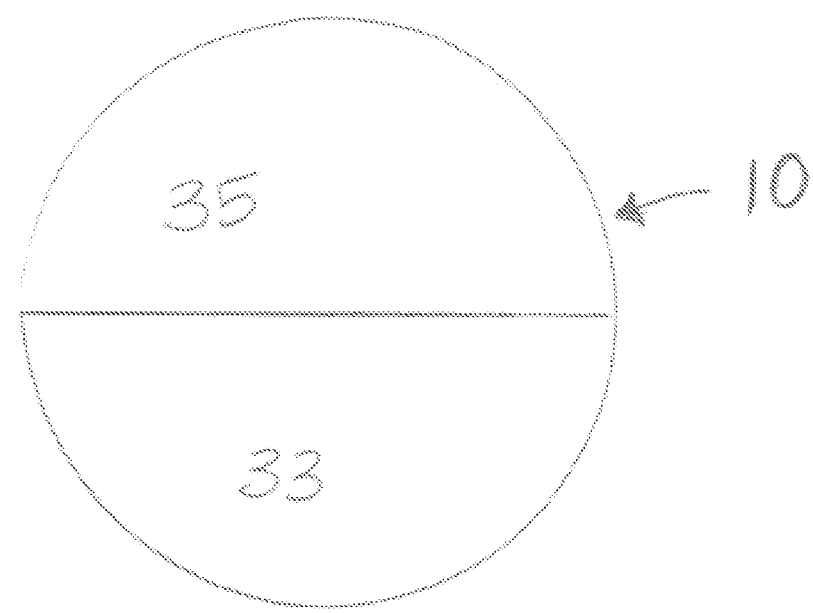
FIG. 2A is a cross section of a portion of an exemplary embodiment of a lead in accordance with the invention.
Figure 2B:
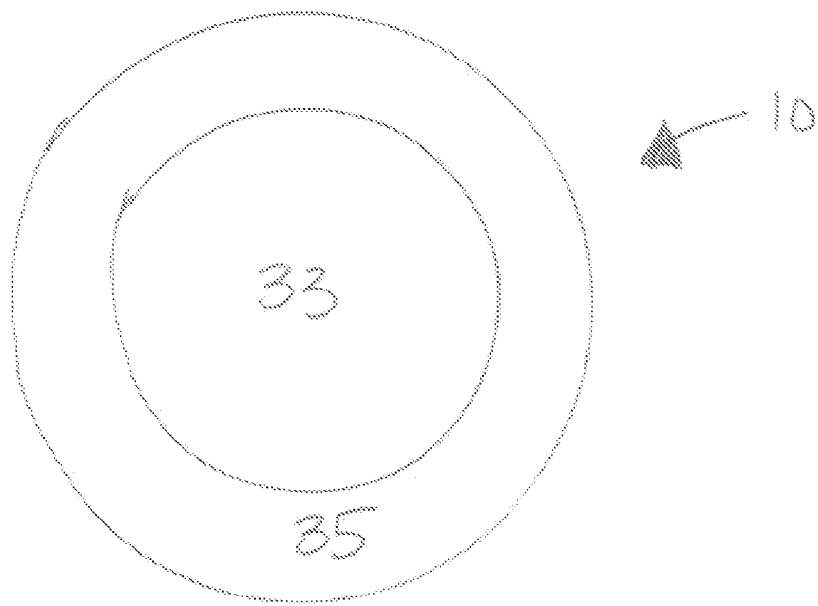
FIG. 2B is a cross section of a portion of another exemplary embodiment of a lead in accordance with the invention.
Figure 2C:
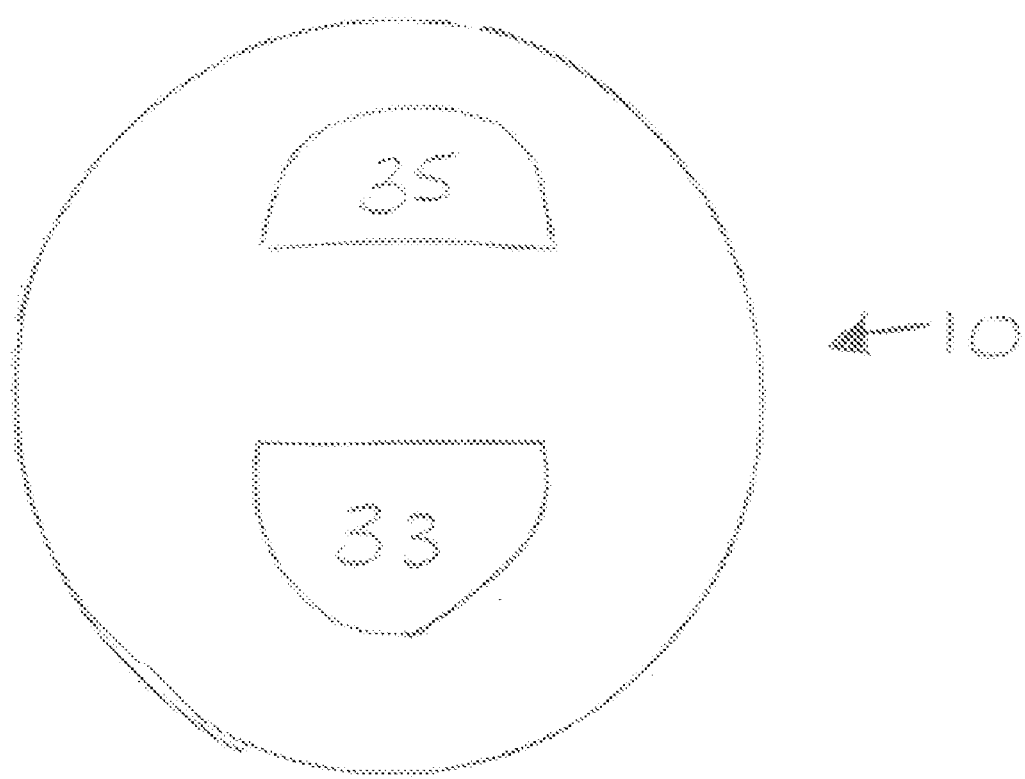
FIG. 2C is a cross section of a portion of yet another exemplary embodiment of a lead in accordance with the invention.

In one embodiment of the invention depicted in FIG. 2A, at least a portion of the lead body may be at least bifurcated with an electrical conduit 33 for electrical components and a fluid conduit 35 that can function as a conduit for fluid flow between the modifiable portion and outside the lead. Although depicted as such in FIG. 2A, the two sections need not be equal in size. It should also be understood by one of skill in the art, having read this specification, that there can be one or more portions of the inside of the lead 10 that houses neither electrical nor fluid components. An example of such an embodiment is depicted in FIG. 2C. Another possible embodiment of a lead in accordance with the invention is depicted in FIG. 2B. In this exemplary embodiment the electrical conduit 33 is inside the fluid conduit 35. Again, one of skill in the art, having read this specification, will understand that the size of the electrical conduit 33 and the fluid conduit 35 need not be equal, or proportional to the sizes depicted in FIG. 2A, 2B, or 2C.

It will also be understood by one of skill in the art, having read this specification, that the cross section of the lead, as depicted in FIGS. 2A, 2B, and 2C, need not be the same throughout the entire length of the lead. In one embodiment, a lead in accordance with the invention has one cross section in the portion of the lead that is proximal to and includes the modifiable portion and another cross section in the portion of the lead that is distal to the modifiable portion.

The modifiable portion has a deflated configuration and an inflated configuration. The modifiable portion is transitioned from the deflated configuration to the inflated configuration via introduction of fluid into the modifiable portion. As mentioned above, the fluid can be introduced via the fluid conduit 35 of the lead 10. Any fluid that can be transmitted to the modifiable portion via the fluid conduit 35 can be utilized. The fluid that is utilized can include both gases and liquids. Exemplary fluids include, but are not limited to, ambient air, nitrogen, carbon dioxide, oxygen; as well as water, saline, silicone, mineral oil, vegetable oil or de-ionized water. In one embodiment of the invention, the fluid can include a visualization agent that will cause the fluid to be visualized with one or more visualization techniques. Examples of visualization agents that can be added to the fluid include, but are not limited to radio-opaque agents, or MRI contrast agents.

In one embodiment of the invention, the fluid conduit 35 can communicate with an area outside the lead via a port. Examples of such ports include a self-sealing septum, or a valve. In one embodiment utilizing a self-sealing septum, a syringe can be used to pierce the septum, and force the fluid into the fluid conduit 35 to inflate the modifiable portion. In such an embodiment, a syringe can also be used to remove the fluid from the fluid conduit 35, thereby transitioning the modifiable portion from the inflated configuration to the deflated configuration. One of skill in the art, having read this specification, would be aware of other methods and tools useful for introducing fluid into the fluid conduit 35, and therefore, the invention contemplates the use of such tools and/or methods.

In one embodiment of the invention, the lead body may include multiple internal lumens, for example, there could be a lumen for the lead conductors, a lumen for a stylet, and a fluid lumen that has a fluid communication with the internal volume of the modifiable portion. In one embodiment, the modifiable portion can be a balloon that is secured to the lead body and that is in fluid communication with the fluid lumen, for example the fluid lumen could have a hole in the balloon to access the internal volume of the balloon. In such an embodiment, fluid forced into the fluid lumen in the lead body at the external, proximal portion of the lead via a port will inflate the balloon subcutaneously and provide fixation. In such an embodiment, the balloon can be made of a biocompatible polymer material and be affixed to the lead body via solvent welding or biocompatible adhesives for example.

In another embodiment, the fluid conduit communicates with a source of fluid that is within the lead itself. In such an embodiment, a larger balloon area at the proximal region of the fluid conduit becomes the source of fluid. In such an embodiment, the larger balloon area in the proximal area of the fluid conduit becomes the source of fluid to transform the modifiable portion from its deflated configuration to its inflated configuration. In one embodiment, the balloon area at the proximal area of the fluid conduit is more elastic than the modifiable portion.

Figure 3A:
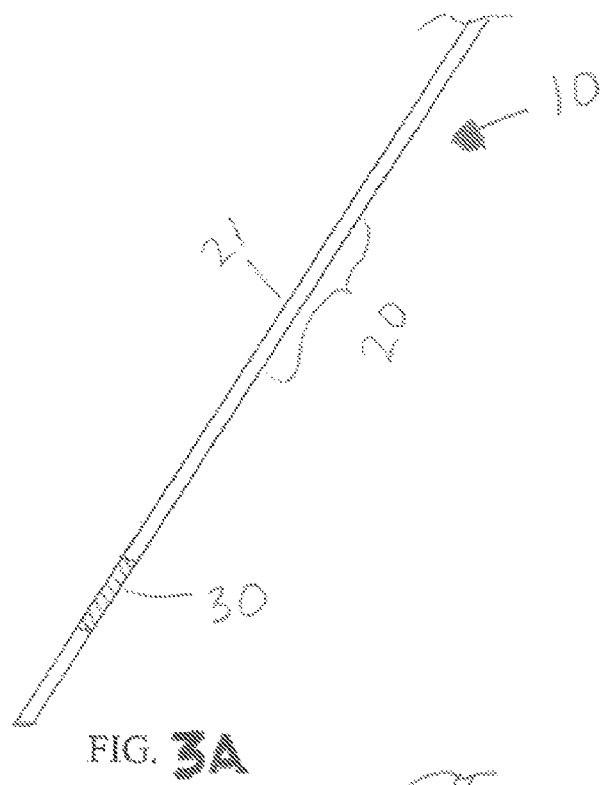
FIG. 3A is an exemplary embodiment of a portion of a lead in accordance with the invention while the modifiable portion is in a deflated configuration.
Figure 3B:
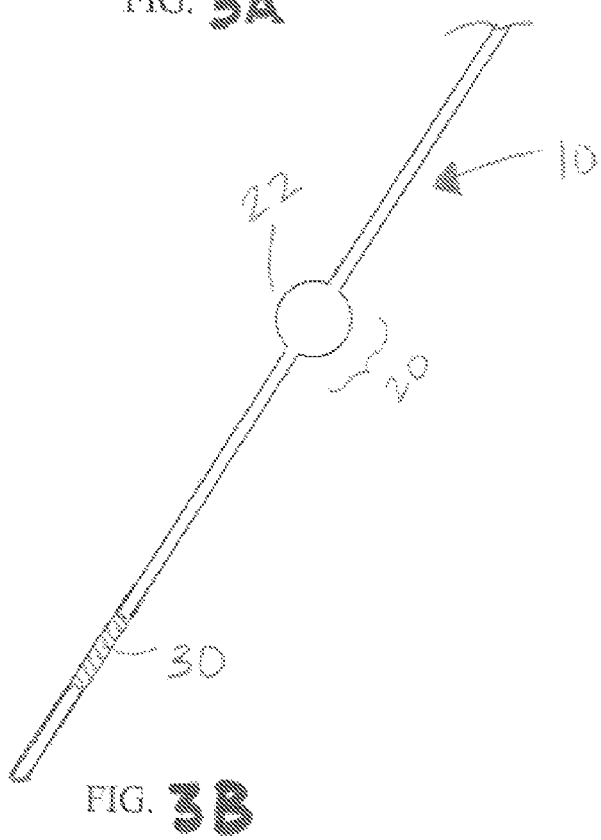
FIG. 3B is the lead depicted in FIG. 3A while the modifiable portion is in an inflated configuration.

FIGS. 3A and 3B offer an example of a lead 10 while having a deflated configuration (FIG. 3A) and while having an inflated configuration (FIG. 3B). As seen there, the modifiable portion 20 goes from having a diameter that is substantially equal to or less than the lead body to a diameter that is substantially greater than the lead body diameter. Fixation with a somewhat malleable structure such as the inflated configuration may provide an advantage because it would be more able to adapt to any type of tissue or surrounding structure.

One of skill in the art, having read this specification, will understand that the inflated configuration need not have a spherical configuration, but could instead have other configurations. Examples of such other configurations include, but are not limited to, cylindrical, irregularly shaped, or elongated ellipses.

In one embodiment of the invention that is designed to be used for implantation within the pelvic floor for sacral nerve stimulation, the lead may be configured so that the inflated configuration lies in close proximity to the foramen after the lead is implanted. In another embodiment of the invention that is designed to be used for implantation within the pelvic floor for sacral nerve stimulation, the lead may be configured so that the inflated configuration forms within the foramen. Such a lead could allow the inflated configuration to act against the bone and the inside of the foramen, or on either side of the facial layer covering the foramen to further anchor the lead where it is implanted.

Figure 4A:
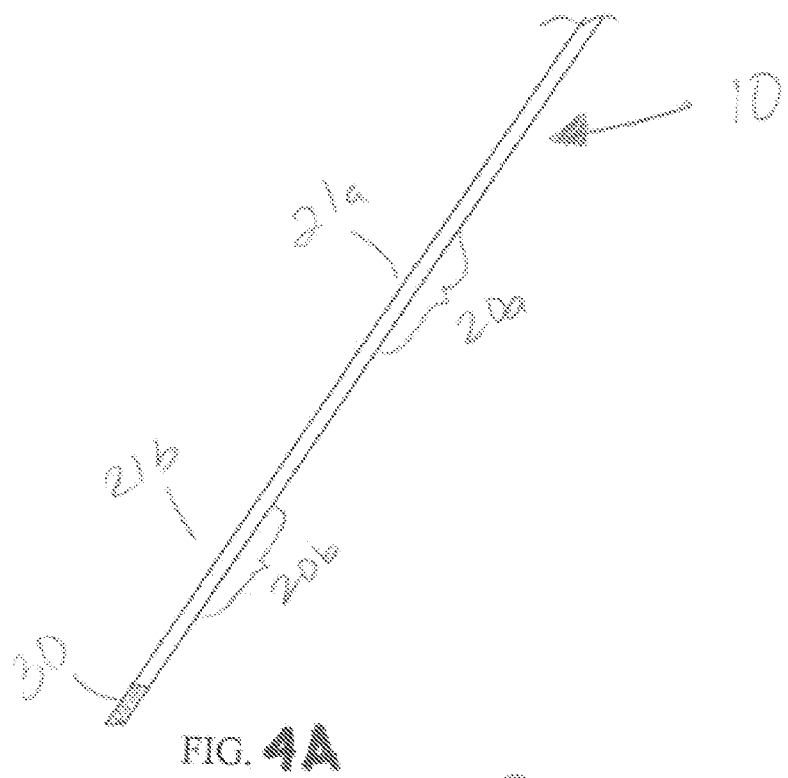
FIG. 4A is another exemplary embodiment of a portion of a lead in accordance with the invention while the modifiable portion is in a deflated configuration.
Figure 4B:
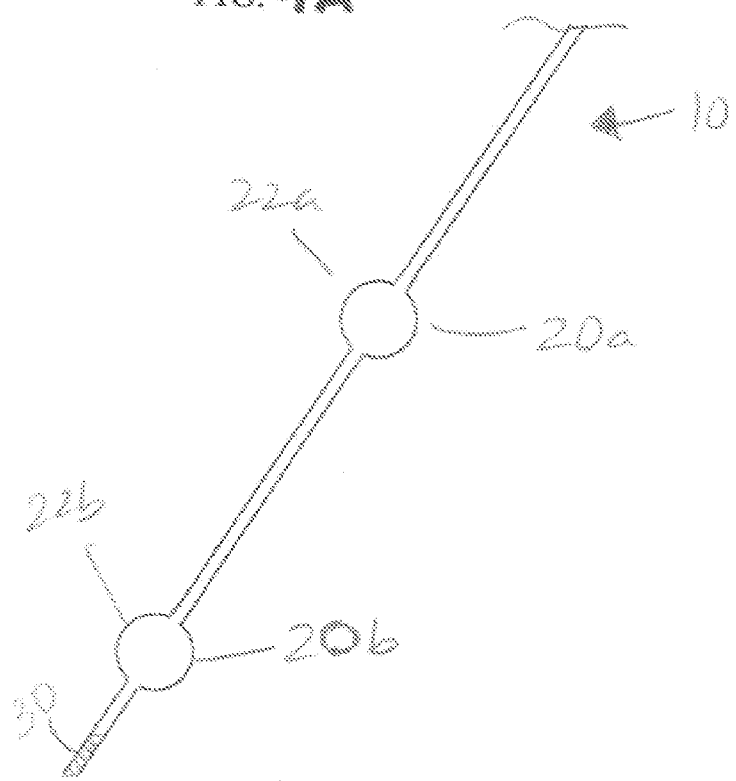
FIG. 4B is the lead depicted in FIG. 4A while the modifiable portion is in an inflated configuration.

FIGS. 4A and 4B offer another example of a lead 10 exhibiting two modifiable portions in deflated configurations (FIG. 4A) and in inflated configuration (FIG. 4B).

In one embodiment, a lead of the invention can include at least two modifiable portions, one of which is located distal the at least one electrode and one that is proximal the at least one electrode. In one embodiment, one of the modifiable portions can be at the most distal tip of the lead, and a second modifiable portion can be proximal the at least one electrode.

Figure 5:
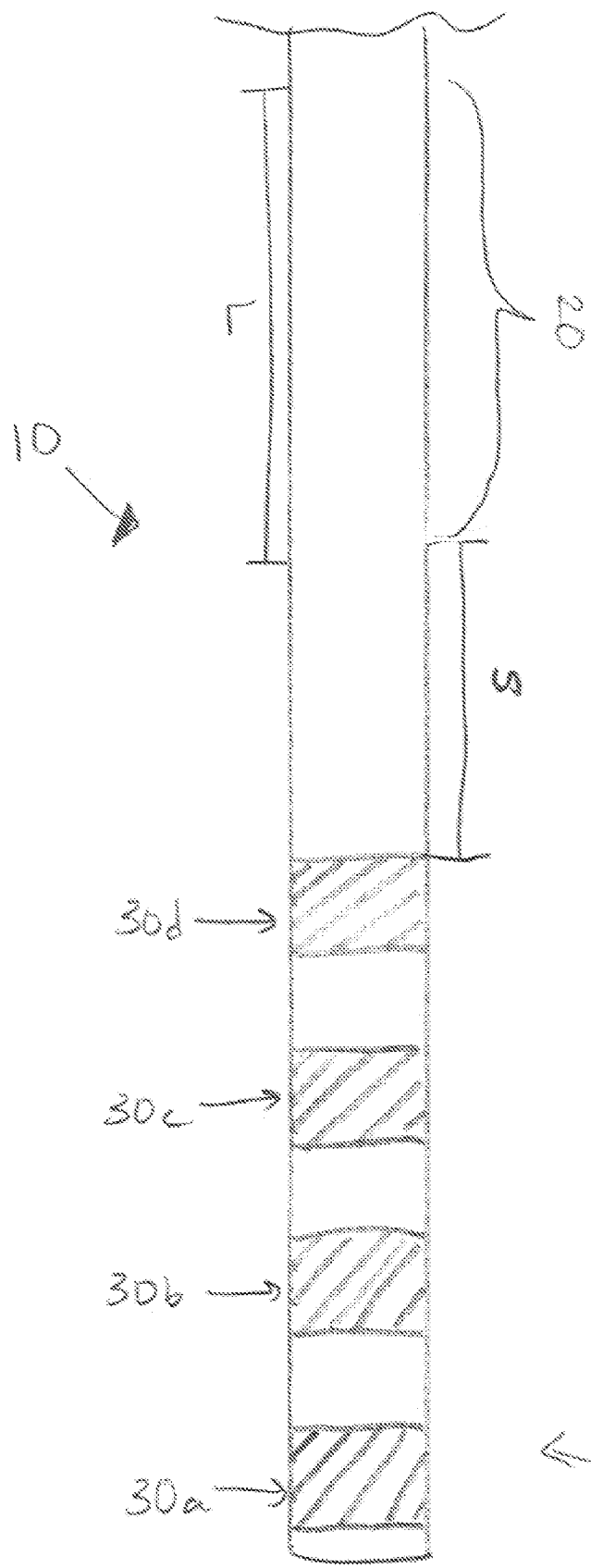
FIG. 5 is a diagram illustrating a portion of a lead in accordance with the invention.

FIG. 5 depicts another exemplary embodiment of a lead 10 in accordance with the invention. As seen in FIG. 5, a lead 10 in accordance with the invention has a spacer distance s between the modifiable portion and the most proximal electrode. In leads having more than one modifiable portion, the spacer distance s between the most proximal electrode and the first modifiable portion and the spacer distance s between the first modifiable portion and the second modifiable portion need not, but can be the same. One of skill in the art, having read this specification, will understand that whether or not the spacer distances s are the same, can depend at least in part on considerations such as, the type of tissue that the lead is to be implanted in, the surrounding anatomy where the lead will be implanted, the particular configuration of the second configuration of the modifiable portion, the number of modifiable portions within the lead, and the location of the at least one modifiable portion within the lead.

In one embodiment, spacer distance s can range from about 1 mm to about 20 mm. In another embodiment, spacer distance s can range from about 5 to about 15 mm. In yet another embodiment, spacer distance s is about 10 mm. One of skill in the art, having read this specification, will understand that any particular spacer distance s can vary depending at least in part on considerations such as, the type of tissue that the lead is to be implanted in, the surrounding anatomy where the lead will be implanted, the particular configuration of the second configuration of the modifiable portion, the number of modifiable portions within the lead if there is more than one, and the location of the one or more modifiable portions within the lead.

As described above, a lead 10 may include at least one modifiable region 20 to fix the lead in any tissue surrounding the lead, such as tissue within an epidural region or tissue within or near a foramen 14 of sacrum 16 for example. At least one modifiable region 20 may be located between electrodes 30 at a distal end of lead 10, or at a proximal end of lead 10. In one embodiment, at least one modifiable region 20 may be disposed proximal to the electrode 30 near the distal end 31 of lead 10 in order to fix the electrodes in place relative to a target stimulation site. In one embodiment, a lead in accordance with the invention may have more than one modifiable region 20. In one embodiment of the invention, a lead of the invention may have 1, 2, 3, 4, or more modifiable regions.

When manufacturing a lead in accordance with this invention, the lead body, including the one or more electrode(s), the one or more modifiable portion(s), and any other features of the lead can be manufactured as was known to one of skill in the art, having read this specification, at the time of the invention.

Figure 6:
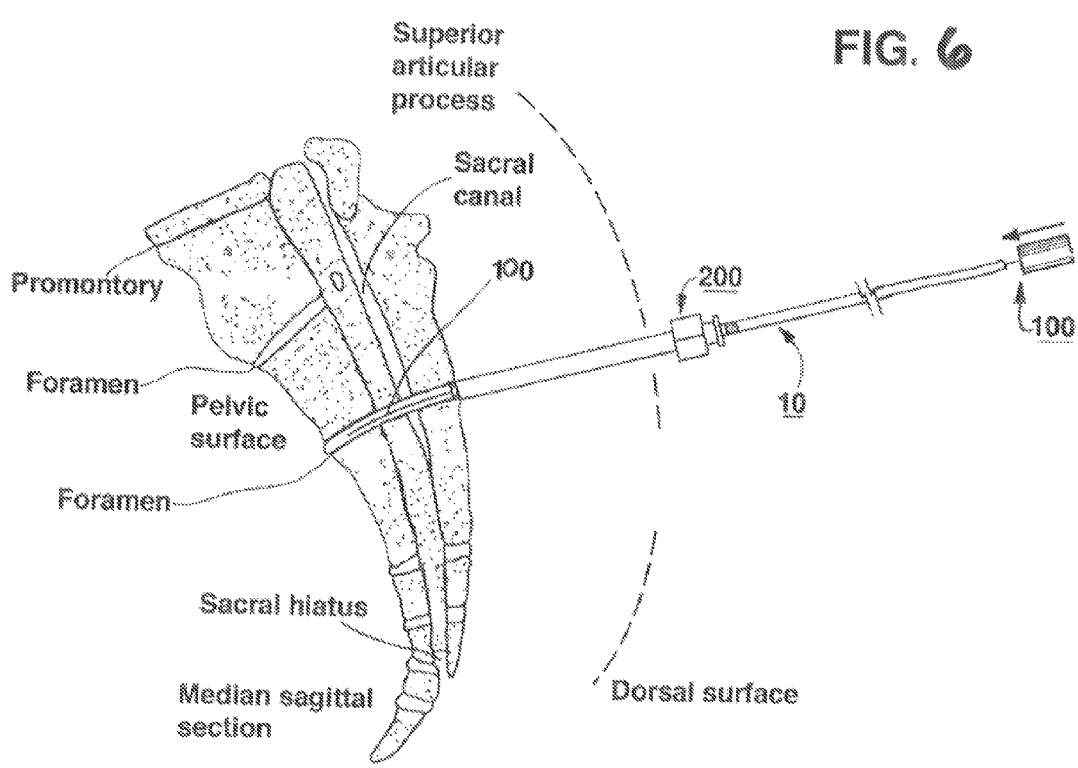
FIG. 6 is a cross-section view of the sacrum schematically illustrating an initial step of implanting a lead of the invention with the modifiable portion in a deflated configuration.

FIGS. 6-9 depict the primary steps of implanting the sacral nerve stimulation lead 10 of the invention. An introducer 200 receives the distal portion 31 of the lead including the at least one electrode 30 and the at least one modifiable portion disposed within the lumen of the introducer 200. A stylet 100 can be disposed within the lead body lumen so that its distal tip closes the lumen distal end opening. The assembly can be advanced percutaneously at a selected angle until the introducer distal end is disposed at the selected foramen as shown in FIG. 6.

To determine the best location of the one or more electrodes, an insulated needle with both ends exposed for electrical stimulation can be used to locate the foramen and locate the sacral nerve by applying electrical stimulation through the needle using an external pulse generator. The efficacy of the location is tested by evaluating the physiologic response in relation to the electrical threshold energy required to elicit the response. For control of urinary incontinence, the physician can implant the medical electrical lead 10 near the S3 sacral nerves. The implantable medical electrical lead 10 may, however, be inserted near any of the sacral nerves including the S1, S2, S3, or S4, sacral nerves accessed via the corresponding foramen depending on the necessary or desired physiologic response.

The advancement of the introducer 200 can be accomplished separately over a guide wire previously percutaneously advanced from the skin incision into the foramen to establish the angle of advancement. Also, a two-part introducer can be employed having an inner introducer element that may be first advanced to the site by itself or over a previously introduced guide wire, and an outer introducer can be introduced over the inner element to dilate the tissue, whereupon the inner element is removed. Any percutaneous introduction tools and techniques may be employed that ultimately provides the introducer 200 in the location depicted in FIG. 6.

The lead 10, optionally stiffened by the stiffening stylet 100 disposed in the lead lumen, is advanced through the introducer lumen proximal end opening into the introducer lumen. However it is accomplished, the at least one electrode 30 and the at least one modifiable portion 20 are disposed within the introducer lumen pre-positioned to be implanted in relation to the sacral nerve accessed through the foramen and in the subcutaneous tissue, respectively.

Figure 7:
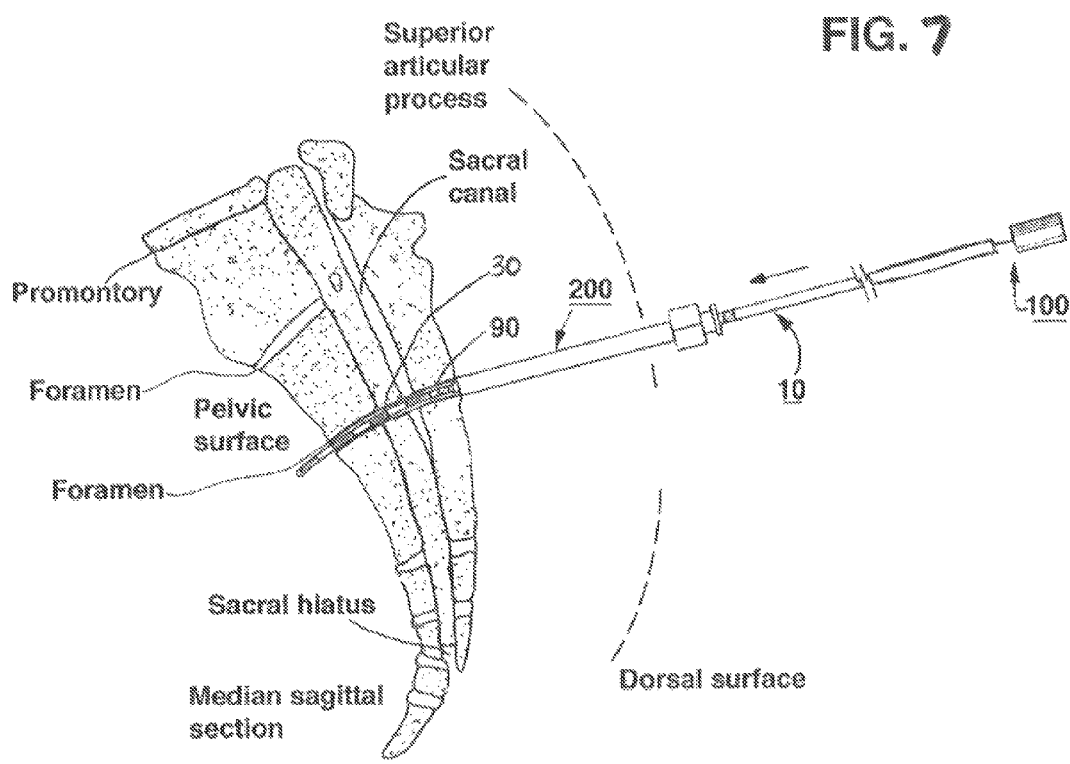
FIG. 7 is a cross-section view of the sacrum schematically illustrating a further step of implanting a lead of the invention extending the one or more electrodes through a foramen.

The stylet 100 may be advanced distally through the foramen as depicted in FIG. 6 or the lead 10 and the stylet wire 100 can both be advanced distally out of the introducer lumen distal end opening to advance the at least one electrode 30 into or through the foramen from the posterior entrance into casual contact with the more anterior sacral nerve as shown in FIG. 7.

Figure 9:
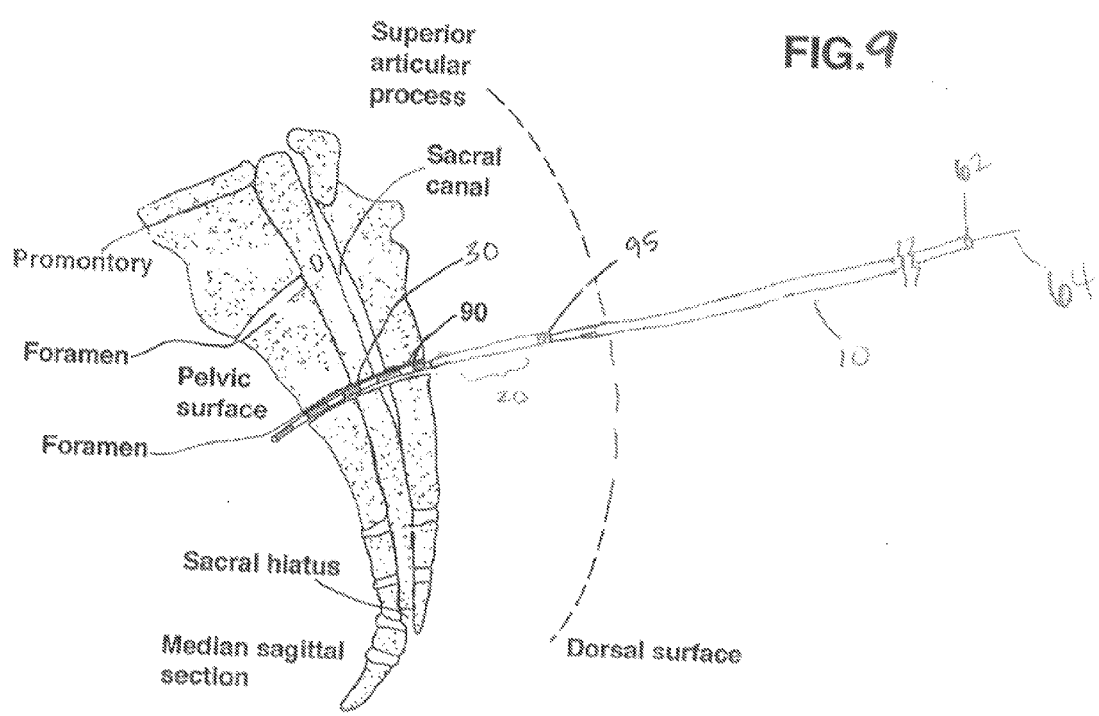
FIG. 9 is a cross-section view of the sacrum schematically illustrating a further step of implanting a lead of the invention after the introducer is fully retracted and while a port is communicating with an outside source of fluid.
Figure 10:
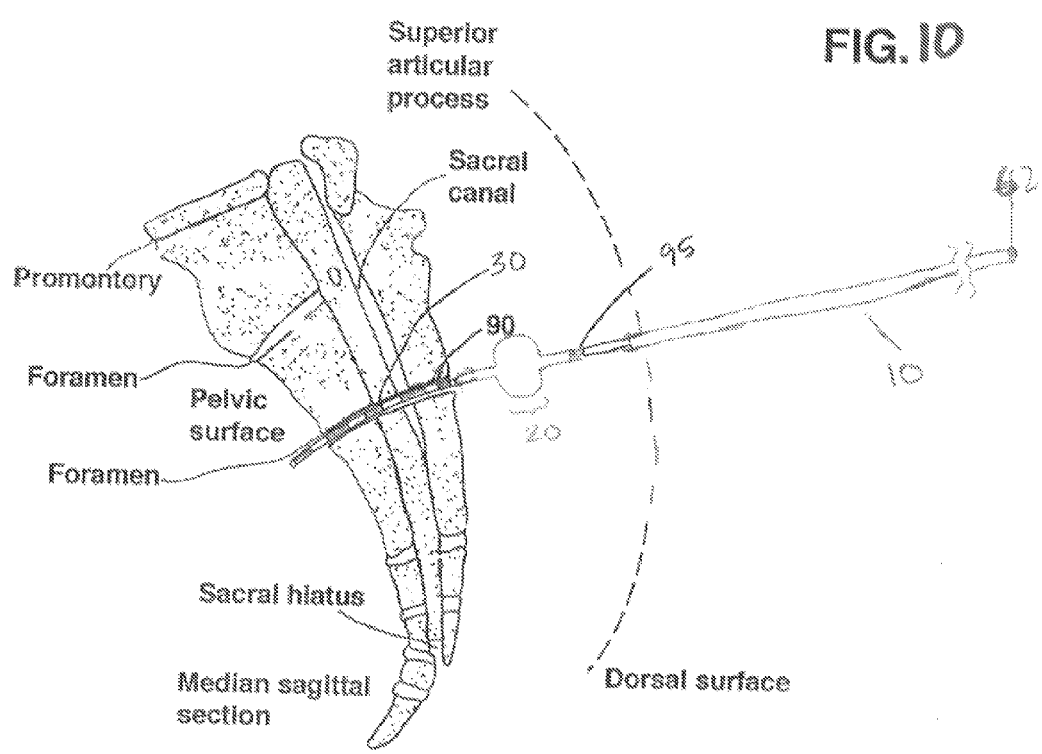
FIG. 10 is a cross-section view of the sacrum schematically illustrating a further step of implanting a lead of the invention after the modifiable portion has been inflated.

After electrical testing to establish optimal positioning is completed the introducer 200 is retracted proximally. The introducer 200 and lead stylet 100, if present, are completely removed, as shown in FIG. 9. The at least one modifiable portion 20 is now transitioned from the deflated configuration to the inflated configuration. In one embodiment, this can be accomplished by introducing fluid into the fluid conduit 35 via a port. For example, as shown in FIG. 9, the fluid could be introduced into a self-sealing septum 62 via a syringe 64. Introduction of the fluid transitions the modifiable portion from the deflated configuration to the inflated configuration, as shown in FIG. 10.

Figure 11:
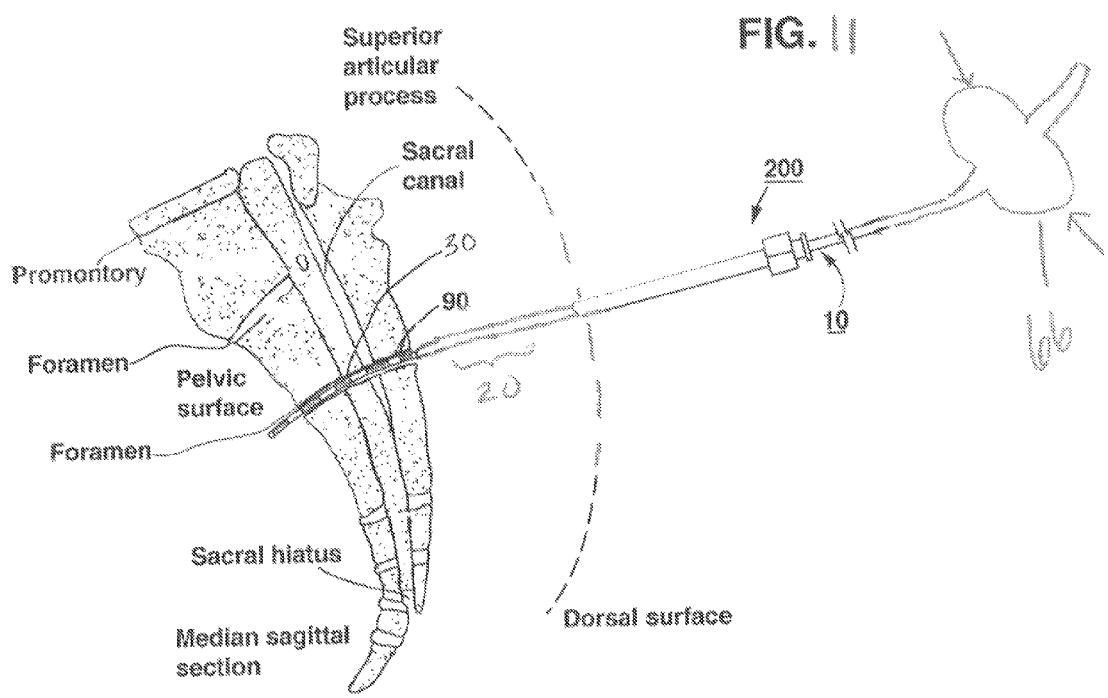
FIG. 11 is a cross-section view of the sacrum schematically illustrating a lead of the invention having a fluid balloon at the proximal end of the lead as the source of fluid for the modifiable portion.
Figure 12:
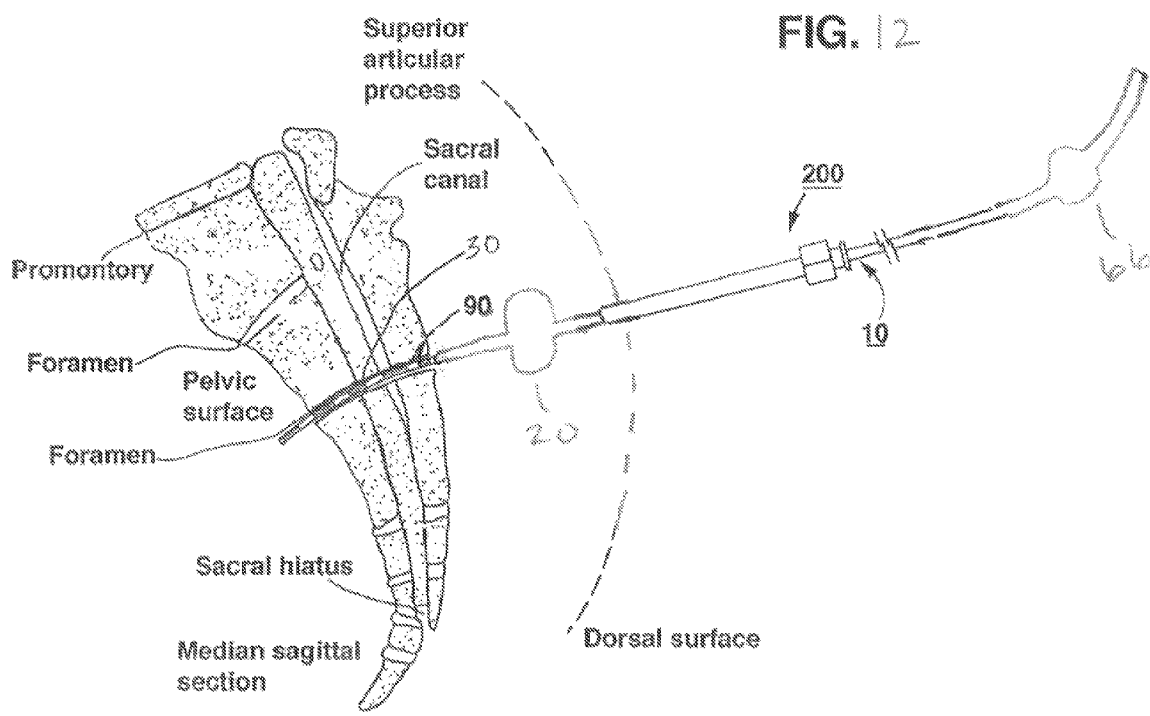
FIG. 12 is a cross-section view of the sacrum schematically illustrating the lead of FIG. 11 with the modifiable portion partially inflated.
Figure 13:
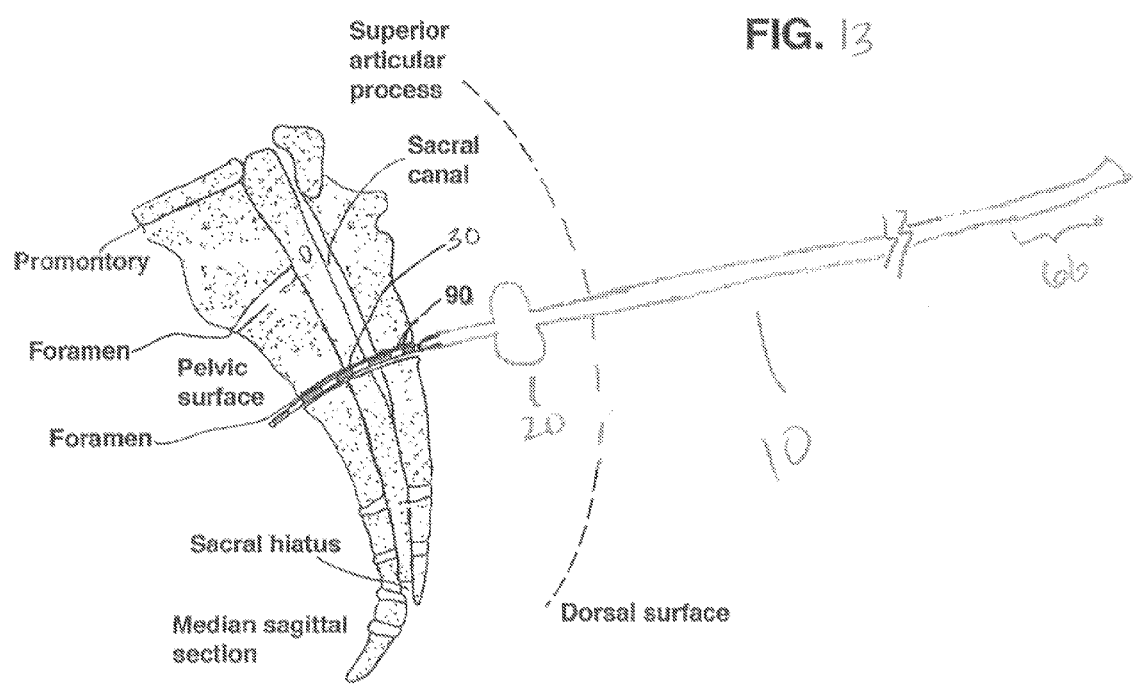
FIG. 13 is a cross-section view of the sacrum schematically illustrating the lead of FIG. 11 with the modifiable portion fully inflated after the introducer has been removed.

In an embodiment that has another balloon area, referred to herein as the fluid balloon 66 at the proximal region of the fluid conduit (an example of which is depicted in FIG. 11) the modifiable portion is transitioned from the deflated configuration to the inflated configuration by applying pressure to the balloon area at the proximal region. This pressure causes the fluid to travel down the fluid conduit and inflate the modifiable portion, as shown in FIG. 12. Once the modifiable portion is inflated, the introducer 200 can be completely removed, as shown in FIG. 13.

Figure 14:
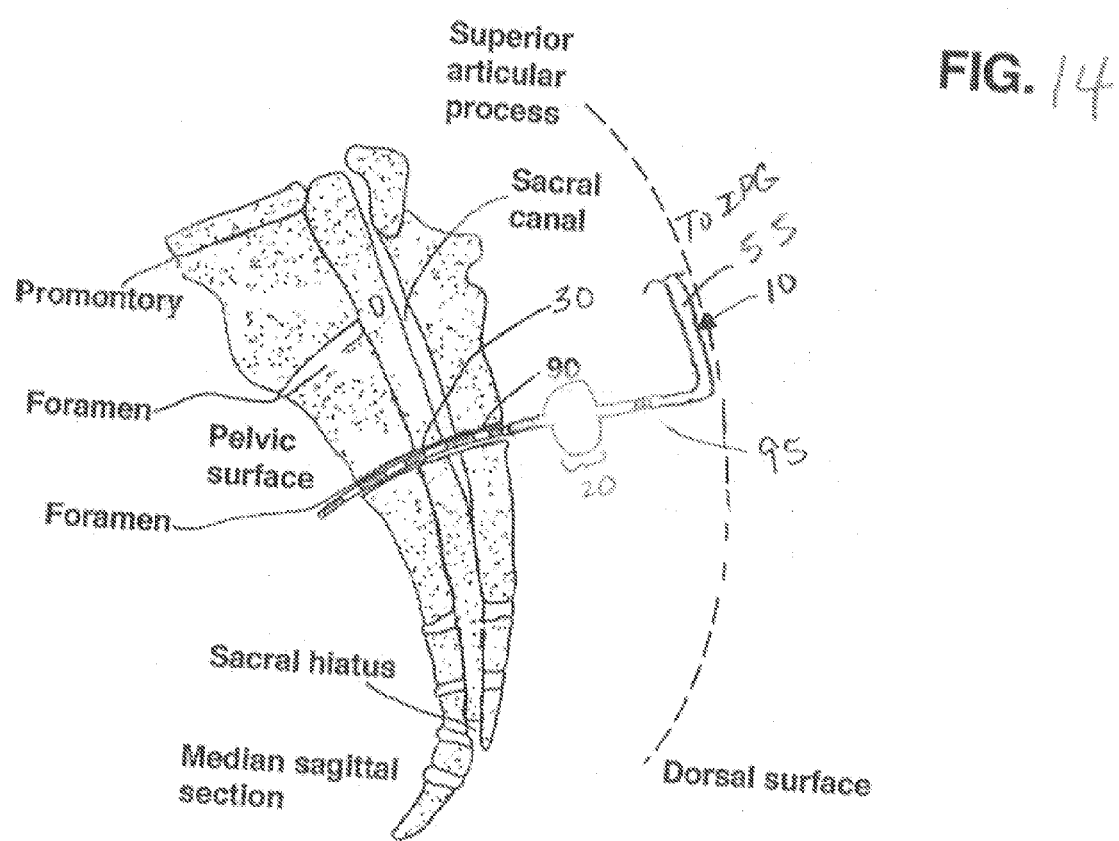
FIG. 14 is a cross-section view of the sacrum schematically illustrating a further step of implanting a lead of the invention subcutaneously routing the proximal portion of the lead body to the implantation site of the neurostimulator IPG.

Once the modifiable portion is inflated, as depicted in either FIG. 9-10, or 11-13, the proximal portion 55 of the lead 10 is bent laterally with respect to the distal portion of the lead 10 and implanted through a subcutaneously tunneled path to the neurostimulator IPG, as shown in FIG. 14.

The lead 10 of the invention also offers the possibility of transitioning the modifiable portion 20 back into the deflated configuration and repositioning the lead 10 within the patient. To do this, the fluid is removed via the fluid conduit 35 to transition the modifiable portion into the deflated configuration. The lead can then easily be repositioned and the fluid can be reintroduced via the fluid conduit 35 to transition the modifiable portion into the inflated configuration again. Such a sequence of steps could also be utilized if or when the lead 10 is to be permanently removed. Returning the lead 10 to its deflated configuration may decrease damage to surrounding tissue when the lead is removed.

Figure 8:
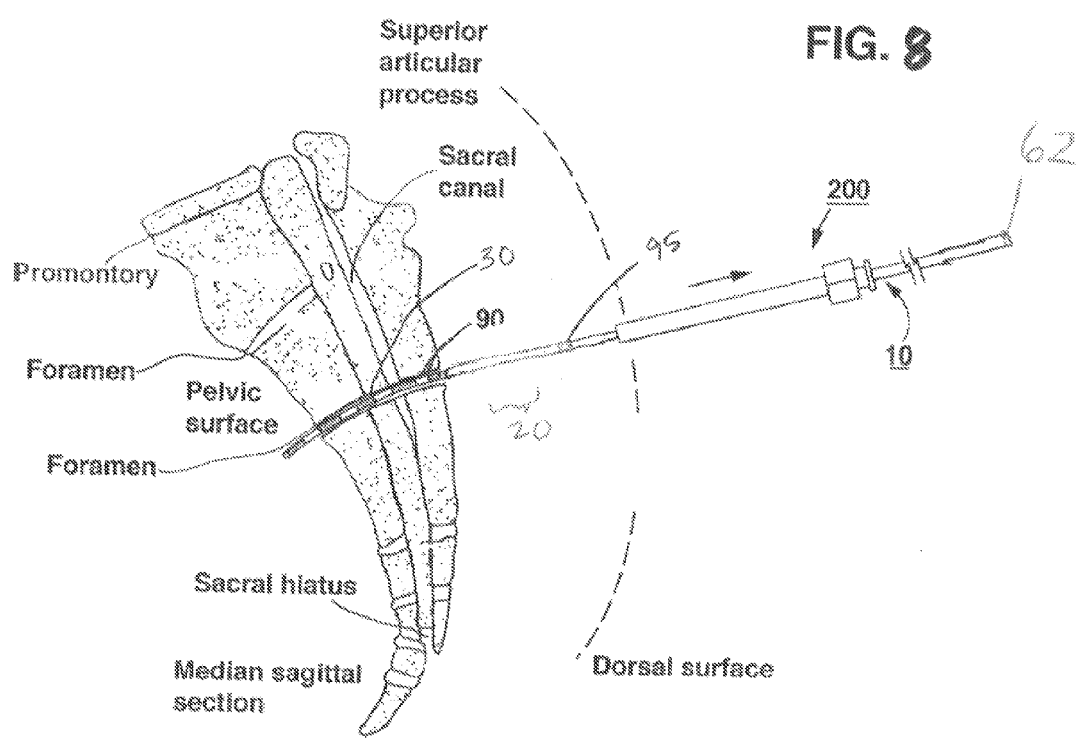
FIG. 8 is a cross-section view of the sacrum schematically illustrating a further step of implanting a lead of the invention retracting the introducer.

In one embodiment of the invention, a lead 10 can include one or more markers, of which marker 90 is an example. Such markers can be made of materials that can be visualized under fluoroscopy. This can allow the physician to more easily see where the particular parts of the lead 10 are within the patient. For example, a lead that has a first marker 90 on the distal end of a modifiable portion 20 and a second marker 95 (as seen in FIGS. 8 and 9) on the proximal end of the modifiable portion, can allow the position of the modifiable portion 20 to be easily located within the patient. When the modifiable portion 20 transitions into the inflated configuration, it bears against the tissue and inhibits proximal retraction of the lead body through the subcutaneous tissue if traction is applied to the lead body since the inflated configuration resists inversion, migration, retraction, and displacement in the proximal direction. Leads in accordance with the invention can also provide strain relief between proximal forces (or strains) in the lead body and the desired location of the electrodes.

The medical electrical leads and procedures of the present invention can be used to stimulate multiple nerves or multiple sides of a single nerve bundle. It should also be understood that although sacral nerve stimulation was exemplified herein, the leads of the invention can be used for other types of nerve stimulation. In addition, the medical electrical lead 10 can also be used as an intramuscular lead where the at least one modifiable portion can engage against muscle and assist in preventing dislodgement of the at least one electrode. This may be useful in muscle stimulation such as dynamic gracilo-plasty or stomach stimulation for gastroparesis or obesity.

Although the invention has been described in detail with particular reference to a certain embodiments thereof, it will be understood variations and modifications can be effected within the scope of the following claims. Such modifications may include substituting elements or components which perform substantially the same function in substantially the same way to achieve substantially the same result for those described herein.

We claim:

1. An implantable medical electrical lead for electrical stimulation of body tissue comprising:
   at least one electrode;
   a lead body having a distal end and a proximal end, the at least one electrode being located at the distal end;
   at least one modifiable portion that is attached to the lead body portion at the distal end in proximity to the at least one electrode;
   wherein the at least one modifiable portion can exist in both a deflated configuration and an inflated configuration, and
   wherein the inflated configuration exhibits a greater resistance to movement of the lead within the body tissue than does the deflated configuration and wherein the inflated configuration provides inflation that symmetrically encircles a longitudinal axis of the lead body;
   a balloon area directly attached to the lead body in proximity to the proximal end, wherein the balloon area is configured to pass through an introducer used to implant the implantable medical electrical lead during removal of the introducer;
   a fluid conduit interconnecting the balloon area and the at least one modifiable portion, wherein the balloon area is inflated with fluid while the at least one modifiable portion is deflated and wherein upon application of pressure to the balloon area, the balloon area is deflated while fluid from the balloon area inflates the at least one modifiable portion.

2. The lead according to claim 1, wherein the modifiable portion is coaxial with the lead body.

3. The lead according to claim 1, wherein the modifiable portion is made of silicone, polyamide, or polyurethane.

4. The lead according to claim 1, wherein the modifiable portion is made of polyurethane.

5. The lead according to claim 1, wherein the at least one modifiable portion is from about 3 mm to about 15 mm long.

6. The lead according to claim 1, wherein the at least one modifiable portion is from about 4 mm to about 10 mm long.

7. The lead according to claim 1, wherein the at least one modifiable portion is from about 5 mm to about 7 mm long.

8. The lead according to claim 1, wherein the lead has two or more electrodes.

9. The lead according to claim 1, wherein the lead has at least four electrodes.

10. The lead according to claim 1, further comprising an introducer that is positioned onto the lead body by passing over the modifiable portion in the deflated configuration while the balloon area is inflated, that remains positioned between the modifiable portion and the balloon area during a transition of the modifiable portion to the inflated configuration and a transition of the balloon area from inflated to deflated, and that is removed from the lead body by passing over the deflated balloon area.

11. A kit comprising:
an implantable medical electrical lead for electrical stimulation of body tissue comprising:
at least one electrode;
a lead body comprising at least a fluid conduit;
a balloon area at a proximal location along the leady body and a modifiable portion at a distal location along the lead body, and
an introducer,
   wherein the fluid conduit extends from the balloon area to the modifiable portion,
   wherein the balloon area and the modifiable portion can exist in both a deflated configuration and an inflated configuration,
   wherein the balloon area is in the inflated configuration when the modifiable portion is in the deflated configuration and the balloon area is in the deflated configuration when the modifiable portion is in the inflated configuration and wherein the balloon area is configured to pass through the introducer,
   wherein the inflated configuration of the modifiable portion exhibits a greater resistance to movement of the lead within the body tissue than does the deflated configuration of the modifiable portion, and
   wherein the introducer is positioned onto the lead body by passing over the modifiable portion in the deflated configuration while the balloon area is inflated, remains positioned between the modifiable portion and the balloon area during a transition of the modifiable portion to the inflated configuration and a transition of the balloon area from inflated to deflated, and is removed from the lead body by the deflated balloon area passing through the introducer.

12. The kit according to claim 11, wherein the modifiable portion is made of silicone, polyamide, or polyurethane.

13. The kit according to claim 11, wherein the modifiable portion is made of polyurethane.

14. The kit according to claim 11 further comprising fluid for introduction into the fluid conduit.

15. The kit according to claim 14, wherein the fluid is saline, de-ionized water, or biocompatible oil.

16. The kit of claim 11, wherein an elasticity of the balloon area is greater than an elasticity of the modifiable portion.

17. The kit according to claim 11, wherein the inflated configuration provides inflation that symmetrically encircles a longitudinal axis of the lead body.

18. A medical electrical stimulation system comprising:
an implantable pulse generator for providing medical electrical stimulation; and
an implantable medical electrical lead for electrical stimulation of body tissue having a distal end and a proximal end, the proximal end being connected to the implantable pulse generator, the implantable medical electrical lead comprising:
at least one electrode at a first location on the distal end;
a lead body;
at least one modifiable portion at a second location on the distal end, wherein the at least one modifiable portion can exist in both a deflated configuration and an inflated configuration, and wherein the inflated configuration exhibits a greater resistance to movement of the lead within the body tissue than does the deflated configuration;
a balloon area at a location on the proximal end;
a first marker visible by fluoroscopy on a distal end of the modifiable portion and a second marker visible by fluoroscopy on a proximal end of the modifiable portion; and
a fluid conduit interconnecting the balloon area and the at least one modifiable portion, wherein the balloon area is inflated with fluid while the at least one modifiable portion is deflated and wherein upon application of pressure to the balloon area, the balloon area is deflated while fluid from the balloon area inflates the at least one modifiable portion.

19. The medical electrical stimulation system of claim 18, wherein the diameter of the deflated configuration is less than the lead body diameter.

20. The medical electrical stimulation system according to claim 16, wherein the inflated configuration provides inflation that symmetrically encircles a longitudinal axis of the lead body.

* * * * *

UNITED STATES PATENT AND TRADEMARK OFFICE
CERTIFICATE OF CORRECTION

PATENT NO.         : 8,145,323 B2                                    Page 1 of 1
APPLICATION NO.    : 11/380480
DATED              : March 27, 2012
INVENTOR(S)        : Eric H. Bonde It is certified that error appears in the above-identified patent and that said Letters Patent is hereby corrected as shown below:

In the Claims

Column 16, line 38, "claim 16" should read -- Claim 18 --.

Signed and Sealed this
Twenty-ninth Day of October, 2013

Teresa Stanek Rea
*Deputy Director of the United States Patent and Trademark Office*